(12) United States Patent
Powell et al.

(10) Patent No.: US 7,195,071 B2
(45) Date of Patent: Mar. 27, 2007

(54) ENZYME COMPOSITIONS AND METHODS OF USING THESE COMPOSITIONS TO DEGRADE SUCCINOGLYCAN

(75) Inventors: Ronald J. Powell, Duncan, OK (US); Bradley L. Todd, Duncan, OK (US)

(73) Assignee: Halliburton Energy Services, Inc., Duncan, OK (US)

(*) Notice: Subject to any disclaimer, the term of this patent is extended or adjusted under 35 U.S.C. 154(b) by 531 days.

(21) Appl. No.: 10/634,721

(22) Filed: Aug. 5, 2003

(65) Prior Publication Data

US 2005/0032152 A1 Feb. 10, 2005

(51) Int. Cl.
*E21B 43/27* (2006.01)

(52) U.S. Cl. .................... 166/305.1; 435/209

(58) Field of Classification Search ........... 435/209, 435/195, 72; 166/304
See application file for complete search history.

(56) References Cited

U.S. PATENT DOCUMENTS

| | | | |
|---|---|---|---|
| 4,754,809 A | 7/1988 | Van Zanten et al. | 166/246 |
| 5,104,566 A | 4/1992 | Guerin et al. | 510/418 |
| 5,184,679 A | 2/1993 | Lau | 166/278 |
| 5,247,995 A | 9/1993 | Tjon-Joe-Pin et al. | 166/312 |
| 5,251,699 A | 10/1993 | Lau et al. | 166/278 |
| 5,514,792 A | 5/1996 | Knipper et al. | 536/124 |
| 5,555,937 A * | 9/1996 | Fisk et al. | 166/301 |
| 5,566,759 A | 10/1996 | Tjon-Joe-Pin et al. | 166/300 |
| 5,831,042 A | 11/1998 | Knipper et al. | 536/1.11 |
| 2001/0036905 A1* | 11/2001 | Parlar et al. | 507/200 |

FOREIGN PATENT DOCUMENTS

WO WO 200057022 A1 * 9/2000

OTHER PUBLICATIONS

EC 3.2.1.73. IUBMB Enzyme Nomenclature. http://www.chem.qmul.ac.uk/iubmb/enzyme/EC3/2/1/73.html. Accessed Mar. 9, 2006.*
Abe, J et al. An endo-(1-<6)-beta-D-glucanase of Flavobacterium M64 hydrolyzing the octasaccharide repeating unit of succinoglycan to two tetrasaccharides. Agric. Biol. Chem., 1980, 44(8): 1877-1884.*
Harada, T. Determination of the structure of beta-D-glycans from strains of agrobacterium and rhizobium. Methods in Carbohydrate Chemistry. 1994. Volume X: 155-163.*
Dumitrium, S. Polysaccharides in Medicinal Applications. 1996. Marcel Dekker, Inc. pp. 41-42.*
York, GM et al. The Rhizobium meliloti ExoK and ExsH glycanases specifically depolymerize nascent succinoglycan chains. Proc. Natl. Acad. Sci. USA. 1998. 95: 4912-4917.*
K.P. Fayad, et al; "Purification and Properties of a B-1, 6-Glucanase from Streptomyces SP. EF-14, an Actinomycete Antagonistic to Phytophthora SPP."; Applied Microbiology Biotechnology; pp. 117-123, 2001.

* cited by examiner

*Primary Examiner*—Leon B. Lankford, Jr.
*Assistant Examiner*—Susan E. Fernandez
(74) *Attorney, Agent, or Firm*—Robert A. Kent; Baker Botts

(57) ABSTRACT

This invention relates to enzyme compositions and methods of using these enzyme compositions, inter alia, to degrade succinoglycan. In one embodiment, the present invention provides a method of degrading succinoglycan comprising contacting the succinoglycan with an enzyme composition that comprises enzymes that are capable of degrading the linkages between sugar moieties of the succinoglycan.

8 Claims, No Drawings

ENZYME COMPOSITIONS AND METHODS OF USING THESE COMPOSITIONS TO DEGRADE SUCCINOGLYCAN

BACKGROUND OF THE INVENTION

1. Field of the Invention

This invention relates to enzyme compositions and methods of using these enzyme compositions, inter alia, to degrade succinoglycan.

2. Description of the Related Art

Succinoglycan is a heteropolysaccharide polymer composed of many monosaccharide units linked by glycosidic bonds produced as high molecular weight polymers and low molecular weight oligosaccharides by a variety of bacteria genera. Succinoglycan generally comprises glucose, galactose, pyruvate, succinate, and acetate. The exact composition of succinoglycan, however, depends on the microorganism producing it as well as the microorganism cultivation conditions. Generally, succinoglycan is composed of repeating units comprising about one galactose and about seven glucose molecules joined by beta-1,4-, beta-1,3- and beta-1,6-glycosidic linkages and is adorned by acetate, pyruvate and succinyl groups. More specifically, succinoglycan may comprise glucose and, for each about 7 moles of glucose, about 0.9 to about 1.2 moles of galactose and about 0.65 to about 1.1 moles of pyruvate, together with succinate and acetate in molar proportions (for each about 7 moles of glucose) between about 0 and about 2.

Succinoglycan is often used in various industries, inter alia, for viscosifying aqueous fluids. For example, in the personal care product industry succinoglycan may be used to viscosity such products as shampoos and the like. In the upstream energy industry, operations in well bores penetrating subterranean formations often involve the use of viscosified treatment fluids that may comprise succinoglycan. Viscosified treatment fluids may be added to a well bore to facilitate the completion of a specific operation on all or a portion of the well bore, e.g., drilling, fracturing, gravel-packing, and the like. Other commonly used viscosifying additives include various polysaccharides such as xanthan, guar, hydroxyethylcellulose, and the like.

In some applications, after a viscosified treatment fluid has performed its desired function, the fluid may be "broken," meaning that its viscosity is reduced. In certain subterranean applications, breaking the fluid is beneficial to the production process because, inter alia, it likely will speed separation of particulates such as proppant or gravel from the viscosified treatment fluid. Breaking a viscosified treatment fluids is usually accomplished by incorporating "breakers" into the fluids. Traditional breakers include acids, oxidizers, enzymes, and the like. Although useful for reducing the viscosity of a viscosified treatment fluid, breakers oftentimes are not specific to the treatment fluid and may degrade a filter cake formed by a treatment fluid, especially if the filter cake comprises components susceptible to the breaker.

Generally, in a drilling operation, filter cakes will form on the walls of the well bore as a deposition of various residues from subterranean operations such as drilling, fracturing, gravel packing, and the like. Such filter cakes are often tough, dense, substantially water insoluble, and capable of reducing the permeability of the surface on which they have formed. Filter cakes often comprise precipitates such as silicates or calcium compounds. Filter cakes also may comprise compounds referred to above as viscosifying additives, e.g., xanthan, succinoglycan, or another polysaccharide. Although some fluids used in well bore operations do not form filter cakes, these fluids may create conditions analogous to those found within filter cakes. Therefore, the term "filter cake" when used herein also refers to these conditions.

Filter cakes are desirable, at least temporarily, in subterranean operations for several reasons. For one, a filter cake may act, inter alia, to localize the flow of a treatment fluid and minimize fluid loss problems. This is an important function of a filter cake because, inter alia, if too much fluid is lost, the conductivity or permeability of the formation may be damaged. A filter cake may also add strength and stability to the formation surfaces on which the filter cake forms. The filter cake may be beneficial to other well bore operations, for example, hydraulic fracturing and gravel packing. Although desirable for a certain amount of time or application, in order to produce the desirable fluids from the formation, the filter cake generally is removed thereafter. Accordingly, the treatment fluids also, generally comprise an additional component that is capable of degrading the non-succinoglycan components of the filter cake such as acids, oxidizers, or enzymes.

In some instances, it is necessary to break a viscosified treatment fluid without negatively impacting the filter cake and vice versa. In other instances, it would be desirable to be able to break both the viscosified fluid and the filter cake with the same breaker.

SUMMARY OF THE INVENTION

This invention relates to enzyme compositions and methods of using these enzyme compositions, inter alias to degrade succinoglycan.

In one embodiment, the present invention provides a method of degrading succinoglycan comprising contacting the succinoglycan with an enzyme composition that comprises enzymes that are capable of degrading the linkages between sugar moieties of the succinoglycan.

The objects, features and advantages of the present invention will be readily apparent to those skilled in the art upon a reading of the description of the preferred embodiments that follow.

DESCRIPTION OF PREFERRED EMBODIMENTS

This invention relates to enzyme compositions and methods of using these enzyme compositions, inter alia, to degrade succinoglycan.

Moreover, in certain embodiments wherein the compositions and methods of the present invention are used in subterranean applications, the present invention relates to enzyme compositions and methods of using these compositions, inter alia, to reduce the viscosity of subterranean viscosified treatment fluids that comprise succinoglycan and/or break filter cakes that comprise succinoglycan.

Although many of the embodiments of the present invention will be discussed herein in the context of subterranean applications, such discussion is only intended to illustrate a particular application of the enzyme compositions of the present invention. The enzyme compositions of the present invention are suitable for any use wherein it is necessary to degrade succinoglycan. Any limitation of the compositions and methods of the present invention to subterranean uses is an improper narrowing of their applications.

The viscosified treatment fluids of the present invention are fluids that comprise succinoglycan. Such viscosified treatment fluids might also comprise a base fluid as well as other optional additives or agents such as particulates. The base fluid often comprises an aqueous-based fluid such as water, brine, aqueous based foams, or water alcohol mixtures, and the like. In certain embodiments of the present invention succinoglycan may be present in the treatment fluid in the range of from about 0.1% to about 2.0% by weight. In certain preferred embodiments, succinoglycan may be present in the treatment fluid in an amount in the range of from about 0.2% to about 1.0% by weight.

The filter cakes of the present invention may comprise succinoglycan as well as other, components, including for example, acid soluble components like calcium carbonate or polymeric components such as xanthan or starch.

When used in subterranean applications, in some embodiments of the present invention, it is desirable to only break the viscosity of the viscosified treatment fluid that may be used for gravel packing or the like without also degrading the filter cake present in the well bore. In these instances, as it is desirable to maintain the integrity of the filter cake, the breaker used to break the viscosity of the viscosified treatment fluid should not negatively impact the filter cake so as to compromise its integrity or interfere with its desirable functionality in an undesirable manner. In other embodiments, it may be desirable to degrade only the filter cake. In yet other embodiments, it is desirable to break both the viscosified treatment fluid and degrade the filter cake. The enzyme compositions of the present invention are suitable for use in conjunction with each embodiment.

The enzyme compositions of the present invention generally comprise any enzyme that is capable of degrading succinoglycan, e.g., by hydrolysis. Optionally, they may comprise a base fluid and/or other additives. In preferred embodiments, enzymes capable of reacting with any of the linkages between the sugar moieties of succinoglycan are suitable for use in the present invention. Specific examples of suitable enzymes are hydrolase-type enzymes. These enzymes are suitable for all embodiments of the present invention, inter alia, because in instances where it is enzymes will not negatively effect a non-succinoglycan derivative in the filter cake but will effectively, break a viscosified treatment fluid comprising succinoglycan. The enzyme compositions may be in any form including encapsulated particles, particles that are impregnated on a carrier, a solid, a liquid, an emulsion, or any mixture thereof. The particular form suited for a given application will depend on the environment and the use. The enzyme compositions can also be designed to create a delayed break of a viscosified treatment fluid and/or a filter cake, for instance, when the process will involve a long pump time and consequently it is necessary to delay the enzymatic action of the enzyme composition. Examples of delayed forms include encapsulated embodiments and solid embodiments. If immediate enzymatic action is desired, a liquid form may be preferable. In certain embodiments of the present invention, the enzyme compositions may be spray-dried, freeze-dried, and the like. In certain embodiments, the cells capable of producing the enzyme of the enzyme compositions are lyophilized. In certain preferred embodiments, the enzyme compositions of the present invention may be provided in, inter alia, a purified form, a partially purified form, as whole cells, as whole cell lysates, or any combination thereof. One of ordinary skill in the art with the benefit of this disclosure will be able to determine the appropriate form for a given application.

In certain preferred embodiments, the enzyme compositions of the present invention comprise a hydrolase enzyme classification of 3.2, according to the Recommendations of the Nomenclature Committee of the International Union of Biochemistry on the Nomenclature and Classification of Enzymes. In certain embodiments of the present invention, hydrolases of the trans-glycosidase superfamily may be used. In certain preferred embodiments of the present invention, glucanase-type enzymes may be used, such as the beta-glucanases. In certain preferred embodiments of the present invention the enzyme compositions may comprise, inter alia, beta-1,4 glucanases, beta-1,3 glucanases, beta-1, 3;1,4 glucanases, beta-1,6 glucanases or any combination thereof. Another enzyme that may be useful is 1,4-(1,3;1, 4)-β-D-glucan 4-glucanohydrolase. One having ordinary skill in the art, with the benefit of this disclosure, will recognize the enzyme, or mixture of enzymes, to use in the enzyme compositions of the present invention to achieve the desired result.

In one exemplary embodiment of the present invention, the enzyme compositions further comprise glycerol, salts, bactericides, or microbiocides. If used, the glycerol may be added in an amount in the range of from about 10% to about 50%, with water comprising the difference. In certain preferred embodiments, the glycerol may be added up to about 35% by weight of the composition. One having ordinary skill in the art, with the benefit of this disclosure, will recognize the appropriate type and amount of additives that may be used in a particular application.

The enzyme compositions of the present invention also may include any particulate material suitable for subterranean applications. Certain embodiments of the compositions of the present invention may comprise particulate material, both independent of or associated with the enzyme. For example, the enzyme may be impregnated onto or within the particulate so as to create a type of delayed release of the enzyme. As such, the particulate material may function, inter alia, as an enzyme carrier of sorts. This may be suitable, inter alia, in gravel pack operations wherein a delayed break of the filter cake behind the gravel pack may be desirable. Any particulate material suitable for use in conjunction with subterranean applications is suitable for use as the particulate in the compositions and methods of the present invention. For example, natural sand, quartz sand, particulate garnet, glass, ground walnut hulls, nylon pellets, bauxite, ceramics, polymeric materials, or the like are all suitable. Suitable sizes range from about 4 to about 100 U.S. mesh, in certain preferred embodiments the sizes range from about 10 to about 70 U.S. mesh. One having ordinary skill in the art, with the benefit of this disclosure, will recognize the particulate type and size to use in conjunction with the enzyme compositions to achieve a desired result. In certain embodiments, the particulates used may be included in the enzyme composition, inter alia, to form a gravel pack down hole or as or in conjunction with proppant particles used in fracturing operations.

Other suitable additives to the enzyme compositions include but are not limited, to, surfactants, chelating agents, foaming agents, and the like. One of ordinary skill in the art with the benefit of this disclosure will recognize when such additives may be useful in a given application.

The enzyme in the enzyme compositions of the present invention may be present in an amount sufficient to reduce the viscosity of the viscosified treatment fluid. More particularly, the enzymes present in the enzyme compositions of the present invention may be present in an amount in the range of from about 10 units of enzyme per milliliter of enzyme composition to about 300 units of enzyme per milliliter of enzyme composition. In certain preferred embodiments, the enzyme is present in the enzyme compositions in the range of from about 50 units of enzyme per milliliter of enzyme composition to about 150 units of enzyme per milliliter of enzyme composition. As used herein, 1 unit, of enzyme is defined as the quantity of enzyme that will liberate 1 micromole of sugar moieties of the succinoglycan per minute at a pH of about 7 at 25° C. Additionally, the enzyme composition may be altered to a desired concentration, such desired concentration being determined by, inter alia, the amount of succinoglycan to be degraded and environmental factors. In certain embodiments, the quantity of enzyme used can be increased so as, inter alia, to reduce the time required for degradation without interfering with the enzyme substrate reaction or causing unwanted side effects. In certain embodiments of the present invention, the amount or activity of the enzyme in the enzyme compositions may be increased in order, inter alia, to overcome any inhibitors to the enzymes found in the viscosified treatment fluid. One having ordinary skill in the art, with the benefit of this disclosure, will recognize the appropriate enzyme concentration adjustments to make in light of the conditions present in a particular application.

Any methods of applying or introducing the enzyme compositions of the present invention to degrade the succinoglycan in a viscosified treatment fluid and/or a filter cake are suitable for use in conjunction with the present invention. In particular, depending on the conditions of the procedure and the type of operations in which the fluid is used, the enzymes may be internally incorporated in the viscosified treatment fluid, externally applied to the viscosified treatment fluid, or any combination thereof. For applications such as, inter alia, hydraulic fracturing and gravel packing, the enzyme compositions may preferably be incorporated internally in the fluid or onto a particulate used in the process. In one embodiment where the filter cake is to be degraded, the enzyme treatments may be pumped to the location of the treatment zone at a rate sufficient to introduce sufficient enzyme to degrade the succinoglycan in the filter cake. In certain embodiments wherein the succinoglycan in a treatment fluid is to be degraded, the enzyme composition may be added to the viscosified treatment fluid via any known process. Depending on the composition of the filter cake, such methods may also be suitable for degrading the filter cake. To achieve certain beneficial effects of the present invention, the enzyme treatment may be shut in the formation for a time sufficient to reduce the viscosity of the treatment fluid. This shut-in-time may be affected by the environmental conditions of the well bore, such as temperature, pH, and the like. If necessary, the pH of the treatment fluid may be adjusted through the use of acids, bases, or suitable buffers.

Generally, to achieve certain beneficial effects of the present invention, the enzyme compositions of the present invention are utilized in an environment sufficient to allow succinoglycan degradation. More particularly, the enzyme compositions are maintained in an environment that preserves enough of the protein structure and function of the enzyme to effectively react with succinoglycan. One having ordinary skill in the art with the benefit of this disclosure will recognize the appropriate environmental conditions for use in a particular application. In certain preferred embodiments of the present invention, environmental conditions including but not limited to, pH, temperature, and the like, or any combination thereof are adjusted to allow enzyme substrate reaction and prevent enzyme inactivation by, inter alia, protein denaturation. More particularly, in some embodiments, the enzyme compositions or the viscosified treatment fluid, comprising the enzyme composition of the present invention may be used at a pH in the range of from about 2 to about 10, depending on, inter alia, temperature. In certain preferred embodiments, the enzyme compositions or the viscosified treatment fluid comprising the, enzyme composition may be used in the range from about 3 to about 9, depending on, inter alia, temperature. In some embodiments, the enzyme compositions or the viscosified treatment fluid comprising the enzyme composition of the present invention may be used in an environment having a temperature in the range of from about 50° F. to about 200° F., depending on how the enzyme composition is introduced. The suitable pH range may depend on temperature range, used and vice versa. Salt concentration also may have an affect on enzyme activity, and therefore, should be considered.

In certain embodiments of the present invention, additives commonly used in the oil industry may be added to the well bore or formation along with the enzyme compositions. For example, additives that may degrade other components of a filter cake may be added. An acid may be added if the filter cake comprises calcium carbonate, for instance. Other additives may be used that could degrade a polymeric component of a filter cake such as xanthan or starch.

In one embodiment, the present invention provides a method of degrading succinoglycan comprising contacting the: succinoglycan with an enzyme composition that comprises hydrolase-type enzymes.

To facilitate a better understanding of the present invention, the following examples of some of the preferred embodiments are given. In no way should such examples be read to limit the scope of the invention.

EXAMPLES

An enzyme composition of the present invention was added to a succinoglycan viscosified treatment fluid, which is commercially available from Halliburton Energy Services in Duncan, Okla., under the tradename "FLO-PAK," having an initial viscosity of 40.5 cP at room temperature. After 24 hours at 150° F., the viscosified treatment fluid and a control viscosified treatment fluid without the enzyme were cooled to room temperature and the respective viscosities were measured. The viscosity of the control viscosified treatment fluid was measured at 35 cP and the viscosificd treatment fluid to which the enzyme composition was added was 10.5 cP. This example illustrates, inter alia, that the enzyme compositions degrade succinoglycan.

In certain embodiments, it may not be desirable to degrade non-succinoglycan polymeric components in the filter cake, although it is desirable to break a viscosified treatment fluid comprising succinoglycan. The next two examples illustrate, inter alia, that the enzyme compositions of the present invention will not negatively impact such polymeric components.

The effect of the enzyme composition on xanthan, a component of a drill-in fluid filter cake was evaluated. A model xanthan gel, which is commercially available from Halliburton Energy Services, Inc. in Houston, Tex., under the tradename "N-VIS," was prepared having an initial viscosity of 36 cP at room temperature. The enzyme composition was added to the N-VIS and the combination composition was maintained at 150° F. After 24 hours the sample fluid was cooled to room temperature and its viscosity was measured. The viscosity of the sample was measured at 36 cP, which represents no change from the initial viscosity.

The effect of the enzyme composition on starch, a common component of a filter cake, also was evaluated. A model starch gel which is commercially available from Halliburton Energy Services in Houston Tex. under the tradename "N-DRIL HT PLUS," was prepared which had an initial viscosity of 48 cP. The enzyme composition was added and the combination composition was maintained at 150° F. After 24 hours, the sample and a control sample without added enzyme were removed, cooled to room temperature, and then its viscosity was measured. The viscosity of the control sample was 46 cP; the sample to which the enzyme composition was added was 45 cP.

Thus, the present invention is well adapted to carry out the objects and attain the ends and advantages mentioned as well as those that are inherent therein. While numerous changes may be made by those skilled in the art, such changes are encompassed within the spirit and scope of this invention as defined by the appended claims.

What is claimed is:

1. A method of maintaining the integrity of a filter cake while reducing the viscosity of a viscosified treatment fluid comprising succinoglycan comprising:
    providing a viscosified treatment fluid comprising succinoglycan, and an enzyme composition selected from the group consisting of beta-1,4 glucanases, beta-1,3 glucanases, beta-1,3;1,4 glucanases, beta-1,6 glucanases, and combinations thereof;
    providing a wellbore penetrating a subterranean formation wherein a filter cake that does not comprise succinoglycan is present in at least a portion of the wellbore;
    placing the viscosified treatment fluid into the wellbore; and
    allowing the enzyme composition to react with the succinoglycan in the viscosified treatment fluid so as to reduce the viscosity of the viscosified treatment fluid but not degrade the filter cake.

2. The method of claim 1, wherein the filter cake comprises materials chosen from the group consisting of guars, derivatized guars, celluloses, derivatized celluloses, starches, derivatized starches, xanthans, and derivatized xanthans.

3. The method of claim 1 wherein the enzyme composition comprises encapsulated particles or impregnated particles.

4. The method of claim 1 wherein the enzyme composition is a solid, a liquid, an emulsion, or a mixture thereof.

5. The method of claim 1 wherein the enzyme composition is in a purified form, a partially purified form, whole cells, whole cell lysates, or a combination thereof.

6. The method of claim 1 wherein the enzyme composition further comprises glycerol, salts, bactericides, microbiocides, surfactants, chelating agents, or foaming agents.

7. The method of claim 1 wherein at least a portion of the enzyme composition is impregnated on a particulate.

8. The method of claim 1 wherein the enzyme is present in the enzyme composition in an amount in the range of from about 10 units of enzyme per milliliter of enzyme composition to about 300 units of enzyme per milliliter of enzyme composition.

* * * * *